United States Patent
Wu

(10) Patent No.: US 6,268,526 B1
(45) Date of Patent: Jul. 31, 2001

(54) PALLADIUM CATALYZED CARBONYLATION PROCESS UTILIZING AROMATIC SUBSTITUTED ALCOHOLS AND/OR AROMATIC SUBSTITUTED ALKYL HALIDES

(75) Inventor: Tse-Chong Wu, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

(21) Appl. No.: 09/212,925

(22) Filed: Dec. 16, 1998

(51) Int. Cl.$^7$ .............................. C07C 51/12; C07C 69/76
(52) U.S. Cl. ...................... 562/406; 560/103; 560/105; 560/114
(58) Field of Search .......................... 562/406; 560/163, 560/114, 105

(56) References Cited

U.S. PATENT DOCUMENTS

| | | | |
|---|---|---|---|
| 2,859,253 | 11/1958 | Snow | 260/651 |
| 3,228,831 | 1/1966 | Nicholson et al. | 167/53 |
| 3,385,886 | 5/1968 | Nicholson et al. | 260/515 |
| 3,600,437 | 8/1971 | Marshall | 260/520 |
| 3,637,767 | 1/1972 | Alvarez | 260/348 R |
| 3,641,127 | 2/1972 | Farge et al. | 260/516 |
| 3,755,427 | 8/1973 | Adams et al. | 260/515 R |
| 3,896,145 | 7/1975 | Berger et al. | 260/315 |
| 4,150,031 | 4/1979 | Berger et al. | 260/315 |
| 4,158,007 | 6/1979 | Gurien et al. | 260/315 |
| 4,246,164 | 1/1981 | Felder et al. | 260/501.17 |
| 4,264,500 | 4/1981 | Zwahlen | 260/315 |
| 4,981,995 | 1/1991 | Elango et al. | 562/406 |
| 5,315,026 | 5/1994 | Wu | 260/105 |
| 5,315,028 | 5/1994 | Wu | 560/105 |
| 5,322,949 | 6/1994 | Wu | 560/105 |
| 5,322,959 | 6/1994 | Wu | 560/105 |
| 5,482,596 | 1/1996 | Wu | 562/406 |
| 5,536,870 | 7/1996 | Wu | 560/56 |
| 6,093,847 | * 7/2000 | Chaudhari et al. | |

FOREIGN PATENT DOCUMENTS

| | | |
|---|---|---|
| 0284310 | 9/1988 | (EP) . |
| 0338852 | 10/1989 | (EP) . |
| 1565235 | 4/1980 | (GB) . |
| 56356359 | 8/1981 | (JP) . |
| 5995238 | 6/1984 | (JP) . |
| 5995239 | 6/1984 | (JP) . |
| 9830529 | 7/1998 | (WO) . |

OTHER PUBLICATIONS

Morrison et al., "Organic Chemistry", Third Edition, Allyn and Bacon, Inc., Boston 1973, pp. 469–471 and 524–525.
Banthorpe, D. V. et al., "Mechanism of Elimination Reactions. Part XX. The Inessentiality of Steric Strain in Bimolecular Olefin Elimination", J. Chem. Soc., 1960, pp. 4054–4087.
Chem Abstract vol. 30, 1936, Col. 1185.
Robinson, J. Michael et al., "Sterochemistry of the Dehydration of 1,2–Diphenylpropanols via Iodo Intermediates", J. Org. Chem. 1986, vol. 51, pp. 109–111.
Falbe, J., "New Syntheses with Carbon Monoxide", Springer–Verlag Berlin Heidelberg, NY, 1980, pp. 250 et seq.
March, Jerry "Advance Organic Chemistry", Second Edition, McGraw Hill Publishers, 1977, pp. 392–394.
Price et al., "6–Chloro–2–naphthylmethylcarbinol, 6–Chloro–2–vinylnaphthalene and Related Compounds"m, J. Am. Chem. Soc., 1948 vol. 70 pp. 4265–4266.
Hughes, Edward et al., "Reaction Kinetics and the Walden Inversion. Part II. Homogenous Hydrolysis, Alcoholysis, and Ammonolysis of α–Phenylethyl Halides" J. Chem. Soc. 1937, pp. 1201–1208.
Olah, George A., "Friedel–Crafts and Related Reactions", vol. 2, Interscience Pub., 1964, pp. 737–741 and 778.
March, Jerry, "Advance Organic Chemistry", Third Edition, Wiley–Interscience, New York, 1985, pp. 299 and 305.
Morrison et al., "Study Guide to Organic Chemistry", Third Edition, Allyn & Bacon Inc., 1975, p. 171.
March. Jerry, "Advance Organic Chemistry", Second Edition, McGraw Hill Book Company, Publishers, 1977, p. 501.

* cited by examiner

Primary Examiner—Paul J. Killos
Assistant Examiner—Robert W. Deemie
(74) Attorney, Agent, or Firm—Philip M. Pippenger

(57) ABSTRACT

A mixture formed from an aromatic substituted alcohol and/or an aromatic substituted alkyl halide, and a copper-free palladium catalyst is carbonylated with carbon monoxide. Extremely high yields of the desired alpha-substituted carboxylic acid can be obtained in very short reaction periods by use of a palladium catalyst that is formed from a palladium compound with a valence of zero to two and a cycloalkyldiarylphosphine ligand, such as neomenthyl-diphenylphosphine.

35 Claims, No Drawings

PALLADIUM CATALYZED CARBONYLATION PROCESS UTILIZING AROMATIC SUBSTITUTED ALCOHOLS AND/OR AROMATIC SUBSTITUTED ALKYL HALIDES

TECHNICAL FIELD

This invention relates to palladium catalyzed carbonylation reactions that yield aromatic substituted aliphatic acids starting from aromatic substituted alcohols and/or aromatic substituted alkyl halides.

BACKGROUND

Processes for producing aromatic substituted aliphatic acids and their derivatives via palladium catalyzed carbonylation reactions are of great interest. Several palladium catalyzed processes for producing aromatic substituted aliphatic acids from olefins have been described, including those disclosed in GB 1 565 235 (1980), U.S. Pat. No. 5,315,026 (1994), U.S. Pat. No. 5,315,028 (1994), U.S. Pat. No. 5,482,596 (1996), U.S. Pat. No. 5,536,870 (1996), and WO 98/30529 (1998). Another convenient route to aromatic substituted aliphatic acids and their derivatives is a palladium catalyzed carbonylation utilizing aromatic substituted alcohols or aromatic substituted all halides. Such processes have been the subject of previous studies, including those reported in JP Kokoku 56-35659 (1981), JP Kokai 59-95238 (1984), JP Kokai 59-95239 (1984), E.P. 338852A1 (1989), U.S. Pat. No. 4,981,995 (1991), and U.S. Pat. No. 5,322,959 (1994).

Two possible isomers may result from the palladium catalyzed carbonylation reaction, one in which the carboxyl group is bound to the alpha carbon, and one in which the carboxyl group is bound to the beta carbon. When the desired carbonylation product is one isomer, formation of mixtures containing both isomers becomes a problem because they are difficult to separate.

THE INVENTION

The processes provided by this invention convert aromatic substituted alcohols and/or aromatic substituted alkyl halides to carboxylic acids and their derivatives, including esters, salts, racemates, and individual optical isomers. In the processes described herein, formation of the beta-substituted isomer is reduced, such that the product is essentially pure after the initial reaction workup. This exceptionally high reaction regioselectivity is brought about by use as the carbonylation catalyst of a palladium catalyst comprising a cycloalkyldiarylphosphine ligand.

Accordingly, an embodiment of this invention entails forming a mixture from ingredients comprising (i) an aromatic substituted alcohol and/or an aromatic substituted alkyl halide, (ii) a copper-free palladium catalyst comprising a palladium compound in which palladium has a valence of zero to two and a phosphine ligand wherein the ligand is a cycloalkyldiarylphosphine, and (ii) an optional halogen acid. The mixture is heated with CO at a pressure of at least about 1 atmosphere and a temperature from about 25° C. to about 300° C. to form an aromatic substituted aliphatic acid or ester. In other words, this embodiment comprises carbonylating with carbon monoxide a mixture formed from an aromatic substituted alcohol and/or an aromatic substituted alkyl halide, and a palladium catalyst comprising a palladium compound in which palladium has a valence of zero to two and a phosphine ligand wherein the ligand is a cycloalkyldiarylphosphine, optionally with a halogen acid such as aqueous hydrochloric acid or aqueous hydrobromic acid. When an aromatic substituted alcohol is used, the halogen acid is necessary, and at least a major portion of the aromatic substituted alcohol is rapidly converted in situ into an aromatic substituted allyl halide by reaction with the halogen acid. The resultant aromatic substituted alkyl halide is then carbonylated. The product of the reaction is a carboxylic ester or a mixte of a carboxylic acid and its ester when an alcohol is incorporated in the reaction; the ester can be hydrolyzed to give the desired carboxylic acid.

A feature of this invention is that the palladium catalyst used is either a single component (i.e., a cycloalkyldiarylphosphine-ligated palladium compound), or is a composition made from two components, viz. (a) one or a mixture of palladium compounds with a valence from zero to two and (b) cycloalkyldiarylphosphine ligand. The catalyst is thus copper-free. Further, when conducted under aqueous conditions, the product of the reaction is a carboxylic acid, which thus can be produced directly in the process when the desired product is a high purity, alpha-substituted carboxylic acid. In short, the acid can be produced directly without need for further reactions.

Another feature of this invention is that it makes possible the formation of the alpha-substituted isomer in extremely high yields, even though the amount of catalyst can be, and preferably is, extremely small. For example, it is possible to achieve yields of the alpha-substituted isomer of at least about ninety percent in reactions periods of six hours or less, using the foregoing palladium catalyst in amounts corresponding to a ratio of 0.01 mole of palladium compound per mole of aromatic substituted alcohol and/or aromatic substituted halide, or less. Moreover, this invention makes it possible to obtain the product with very high ratios of the alpha-substituted isomer, generally with ratios of alpha to beta isomer of at least about 100:1, and, in preferred cases, in ratios of about 500:1, or more.

The aromatic substituted alcohols and/or aromatic substituted halides in this invention are alkyl halides and alcohols substituted with an aromatic group; preferably, the aromatic group is bound to the 1-position of the alcohol. Typically these compounds have a general formula (1), in which X is a halogen atom or preferably a hydroxy group. When X is a halogen atom, it is an iodine, a bromine, or most preferably, a chlorine atom. The carboxylic compounds produced by the practice of this invention have the formula (II).

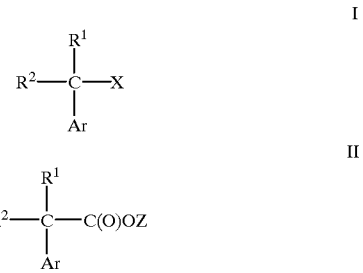

In both formula (I) and formula (II), $R^1$ and $R^2$ are the same or different and are selected from hydrogen atoms, hydrocayl groups, functionaly-substituted hydrocarbyl groups, substituted or unsubstituted aryl groups, and halogen atoms. Examples include compounds of formula (I) wherein $R^1$ and $R^2$ are hydrogen atoms, substituted or unsubstituted phenyl, $C_1$ to $C_6$ alkyl, and/or trifluoromethyl. The preferred compounds of formula (I) are those in which $R^1$ and $R^2$ are hydrogen atoms andlor $C_1$ to $C_6$ alkyl groups. Compounds in which $R^1$ is a hydrogen atom are more preferred; compounds in which $R^1$ is a hydrogen atom and $R^2$ is a $C_1$ to $C_6$ alkyl group are highly preferred. The preferred alkl halide moiety is ethyl halide, and the preferred alcohol moiety is ethanol, which requires in formula (I) that $R^1$ is a hydrogen atom and $R^2$ is a methyl group in the most highly preferred compounds. Aromatic substituted alcohols are the preferred starting materials for the carbonylation reaction.

In formula (II), Z is an alkali metal atom (preferably Na or K) when the acid is neutralized with a suitable base such as NaOH or KOK a hydrocawbyl group (preferably $C_1$–$C_6$ alkyl), a fiictionally-substituted hydrocarbyl group, or, most preferably, a hydrogen atom. By suitable modifications of or additions to the procedures described herein, compounds of formula (II) can be produced in which Z can be any of a wide variety of other groups, nonlimiting exemplifications of which include ammonium, quaternamy ammonium, one-half equivalent of a divalent metal atom, one-third equivalent of a trivalent metal cation, and so forth.

The aromatic group [Ar of formula (I) and formula (II)] is aryl, substituted aryl, heteroaryl, substituted heteroaryl, aralkyl, or substituted aralkyl, encompassing phenyl, naphthyl, biphenyl, carbazolyl, or substituted phenyl, naphthyl, biphenyl, or carbazolyl, with at least one substituent which may be benzoyl, naphthoyl, halogen, amino, nitro, hydroxy, alkyl or alkoxy, the preferred aromatic group depends on the product desired. Examples of substituted aryl groups include isobutylphenyl, methoxynaphthyl, phenoxyphenyl, fluorobiphenylyl, benzoylphenyl, and chlorocarbazolyl.

In highly preferred embodiments, the aromatic substituted alcohols and/or aromatic substituted alkyl halides of choice are 1-(4-isobutylphenyl)ethanol or 1-(4-isobutylphenyl)-ethyl chloride, 1-(3-fluoro-4-biphenylyl)ethanol or 1-(3-fluoro-4-biphenylyl)ethyl bromide, 1-6-methoxy-2-naphthyl)ethanol or 1-(6-methoxy-2-naphthyl)ethyl chloride, 1-(3-phenoxy-phenyl ethanol or 1-3-phenoxyphenyl)ethyl bromide, 1-(3-benzoylphenyl)ethanol or 1-(3-benzoylphenylethyl chloride, and 1-(6-chloro-2-carbazolyl)ethyl bromide or 1-(6-chloro-2-carbazolyl) ethanol which yield, respectively, ibuprofen, 2-(4-isobutylphenyl)propionic acid (U.S. Pat. Nos. 3,228,831 and 3,385,886); 2-(3-fluoro-4-biphenylyl)-propionic acid (also known as flurbiprofen) (U.S. Pat. No. 3,755,427); racemic 2-(6-methoxy-2-naphthyl)-propionic acid which can be resolved to d-2-(6-methoxy-2-naphthyl)-propionic acid (also known as naproxen) (U.S. Pat. No. 3,637,767); a-dl-2-(3-phenoxy-phenyl)propionic acid (also known as fenoprofen) (U.S. Pat. No. 3,600,437); 2-(3-benzoylphenyl) propionic acid (also known as ketoprofen) (U.S. Pat. No. 3,641,127); and 2-(6-chloro-2-9H-carbazolyl)-propionic acid (also known as carprofen) (U.S. Pat. No. 3,896,145 and U.S. Pat. No. 4,158,007).

The present invention embraces the formation of any racemates and individual optical isomers of the compounds of formula (II) having a chiral carbon atom. For example, when compounds of formula (II) wherein the acid is 2-(6-methoxy-2-naphthyl)propionic acid, are subjected to resolution as taught in U.S. Pat. No. 4,246,164 (incorporated herein by reference), the analgesic compound naproxen is produced.

The palladium catalyst can be (1) a palladium catalyst generated in situ from a mixture of one or more palladium compounds having a valence of zero to two and a cycloalkyldiarylphosphine ligand of the following formula (III), or (2) a preformed ligated palladium catalyst in which the palladium has a valence of zero to two and the ligand has formula (III).

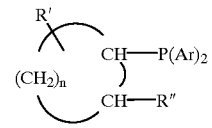

In formula (III), R' and R" are the same or different and are individually hydrogen, alkyl, aryl or substituted aryl; Ar is phenyl, naphthyl, substituted phenyl or substituted naphthyl; and n is an integer from 3 to 6. Preferably, R' and R" are the same or different and are $C_1$ to $C_6$ alkyl Ar is phenyl or naphthyl, and n is 3 or 4. Most preferably, R' is methyl or ethyl, R" is $C_3$ to $C_6$ branched alkyl, Ar is phenyl, and n is 4. Especially preferred as the phosphine ligand is neomenthyldiphenylphosphine.

Active catalytic species are preferably formed in situ by the addition to the reaction mixture of the individual components. One or more palladium compounds and the cycloalkyldiarylphosphine ligand can be added to or included in the reaction vessel separately from each other. In such a case, the palladium compound(s) and the cycloalkyldiarylphosphine ligand can be introduced into the reaction vessel concurrently or sequentially in any order. However, the catalyst can be preformed externally to the reaction mixture and charged to the reactor as a preformed catalyst composition.

The use of salts of palladium in forming the catalysts is preferable because catalyst compositions formed from palladium salts appear to have greater activity than those made from palladium metal itself Inorganic salts may be the palladium salts, and include the chlorides, bromides, nitrates, and sulfates. Organic palladium salts may also be used, and include complexes and salts such as the carboxylates. Examples of palladium compounds include $PdCl_2$, $Pd(OAc)_2$, $Pd(CH_3CN)_2Cl_2$, $PdBr_2$, $Pd(NH_3)_2Cl_2$, $Pd(CH_3CN)_4(BF_4)_2$, tris(dibenzylideneacetone)dipalladium (0) chloroform adduct, and bis(dibenzylideneacetone) palladium(0). Of the salts, Pd(II) halides (chloride, bromide, iodide) and Pd(II) carboxylates (e.g., acetate, propionate, etc.) are most preferred. Thus, for example, palladium(II) chloride or palladium(II) acetate and might be used in the carboxylation, in the most preferred case, $PdCl_2$ and neo-menthyldiphenylphosphine are in fact used. Examples of preformed ligated palladium catalysts include tetrakis (neomenthyldiphenylphosphine)palladium(0), tetrakis (neomenthyldiphenylphosphine)palladium(II) perch-lorate, bis(neomen-thyldiphenylphosphine)palladium(II) chloride, and bis(neomenthyldiphenyl-phosphine)-palladium(II) acetate.

Mixing one or more palladium compounds and cycloalkyldiarylphosphine ligand forms a catalyst. The molar ratio of cycloalkyldiarylphosphine ligand to palladium compound ranges from at least about 1:1 to about 20:1; preferred ratios range from about 2:1 to about 15:1. While it is possible to carry out the reaction using a mole ratio of aromatic substituted alcohol and/or aromatic substituted allyl halide to palladium compound in the range of about 25:1 to 50:1, it is distinctly preferred to employ molar ratios of aromatic substituted alcohol and/or aromatic substituted alkyl halide to palladium compound of at least about 100:1, and more preferably at least to about 500:1. Typically, this ratio can be as high as about 10000:1, but preferably, the ratio does not exceed about 5000:1. Highly preferred a s a carbonylation catalyst is the species formed in situ from the mixture of Pd(II) and/or Pd(0) compound(s) and neomenthyldiphenylphosphine. The use of an aromatic substituted alcohol with the catalys species formed from the mixture of a Pd(II) salt and neomenthyldiphenylphosphine is a particularly preferred embodiment of this invention.

Addition of a halogen acid is necessary when an aromatic substituted alcohol is used. The carbonylation reaction may be performned under initially neutral conditions (i.e., without the added acid) when the starting material is an aromatic substituted alkyl halide. However, the reaction is preferably conducted under acidic conditions with an added halogen acid. A hydrohalide acid is preferred; more preferred is an aqueous hydrohalide acid that may have a concentration up to about 30 weight percent, but preferably has a concentration in the range of about 2 to about 20 weight percent, and more preferably is in the range of about 5 to about 15 weight percent. Suitable halogen acids include aqueous HCl, HBr, or HI. The preferred halogen acid is hydrochloric acid; it is especially preferred to use approximately 10 weight percent aqueous hydrochloric acid.

In the reaction vessel, the partial pressure of carbon monoxide is at least about one atmosphere (0 psig) at ambient temperature or the temperature at which the reaction vessel is charged Higher pressures of CO may be used, up to the limits of said reaction vessel. A pressure up to about 3000 psig is convenient in this process. CO pressures that are preferred range from about 100 psig to about 2500 psig at the reaction temperature, and most preferred is a pressure from about 250 psig to about 2000 psig. It should be noted that the presence of oxygen is undesirable in the carbonylation reaction of this invention. Hence, an atmosphere of 100% carbon monoxide is most preferred to carry out this process. Various inert gases, such as nitrogen or argon, can, however, be incorporated in the reaction mass, the only criterion being that the process should not be slowed to the point of requiring exceptionally long periods to complete the reaction.

The tempe e sufficient to induce carbonylation of the aromatic substituted alcohol or aromatic substituted alkyl halide ranges from about 25° C. to about 300° C. A more useful temperature range is from about 50° C. to 200° C.; preferred temperatures range from about 85° C. to about 150° C.

In order to obtain carbonylated products, the components of the reaction mixture are allowed to contact each other for a time lasting from about thirty minutes to about twenty-four hours. A preferred contact time range is from about one hour to about twelve hours; more preferred is a range from about one hour to about eight hours. Optimum reaction times will vary with the choice of starting material.

The presence of a solvent is not always required in the carboxylation reaction, although it is desirable in some circumstances. When an ester or an alcohol is used as solvent, the product is usually the corresponding ester of the carboxylic acid. Any solvent in which the substances added are soluble, and which do not interfere with the desired reaction may comprise the reaction mixture. Those solvents which can be used include one or more of the following: ketones, for example, acetone, methyl ethyl ketone, diethyl ketone, methyl n-propyl ketone, acetophenone, cyclohexanone, and the like; linear, poly, and cyclic ethers, for example, diethyl ether, di-n-propyl ether, di-n-butyl ether, ethyl n-propyl ether, glyme (the dimethyl ether of ethylene glycol), diglyme (the dimethyl ether of diethylene glycol), tetrahydrofuran, dioxane, 1,3-dioxolane, and similar compounds; and aromatic hydrocarbons, for example, toluene, ethylbenzene, xylenes, and similar compounds. The preferred aromatic hydrocarbon is benzene; the preferred ketone is diethyl ketone. Ethers are also preferred; the most preferred ether is 1,4-dioxane.

The following examples are presented for purposes of illustration, and are not intended to impose limitations on the scope of this invention.

GENERAL DESCRIPTION

Nuclear magnetic resonance (NMR) was used to determine the purity of the GC standard samples of 1-(4-isobutylphenyl)ethyl chloride, 1-(4-isobutylpheyl)ethanol, 1-ethyl-4-isobutylbenzene, 2-(4-isobutylphenyl)propionic acid, and 3-(4-isobutylphenyl)propionic acid. A GC standard sample of 4-isobutylstyrene was not available, but in lieu of the standard, a sample of 1-ethyl-4-isobutylbenzene was used, because the slight difference in molecular weight (2 hydrogen atoms) does not cause a significant difference in the GC analyses. The major components of the heavy ends were identified by GC/MS and the quantity of the heavy ends was calculated using an assumed response factor based on one-half of the average of the 1-ethyl-4-isobutylbenzene and 1-(4-isobutylpheyl)ethanol response factors.

Yields are reported in percent for Tables 1–4. Eicosane was used as a GC internal reference for all the quantitative GC determinations.

EXAMPLE 1

1-(4-isobutylphenyl)ethyl chloride (10.0 g, 97.0 w %, 49.3 mmol), 10% HCl (20.0 g), PdCl$_2$ (9.0 mg, 0.0508 mmol), neomenthyildiphenylphosphine (99.0 mg, 0.305 mmol), and 1,4-dioxane (25 mL) were charged to a 100-mL Hastelloy B autoclave. The autoclave was set up in the hood and purged with CO (3×200 psig). The autoclave was then pressured to 700 psig with CO and the mixture was heated to 115–120° C. for 2 hours. The CO pressure was kept at 900–1000 psig. The result of quantitative GC analysis is shown in Table 1.

COMPARATIVE EXAMPLE 1

The procedure of Example 1 was repeated except that Ph$_3$P (83.0 mg, 0.316 mmol) was used as the ligand. The result of quantitative GC analysis is shown in Table 1.

EXAMPLE 2

1-(4-isobutylphenyl)ethyl chloride (10.0 g, 97.0 w %, 49.3 mmol), 10% HCl (20.0 g), PdCl$_2$ (9.0 mg, 0.0508 mmol, neomenthyldiphenylphosphine (99.0 mg, 0.305 mmol), and diethyl ketone (25 mL) were charged to a 100-mL Hastelloy B autoclave. The autoclave was set up in the hood and purged with CO (3×200 psig). The autoclave was then pressured to 700 psig with CO and the mixture was heated to 115–120° C. for 4 hours. The CO pressure was kept at 900–1000 psig. The result of quantitative GC analysis is shown in Table 2.

COMPARATIVE EXAMPLE 2

The procedure of Example 2 was repeated except that Ph$_3$P(82.0 mg, 0.313 mmol) was used as the ligand. The result of quantitative GC analysis is shown in Table 2.

EXAMPLE 3

1-(4-isobutylphenyl)ethanol (10.0 g, 94.0 w %, 52.7 mmol), 10% HCl (20.0 g), PdCl$_2$ (9.3 mg, 0.0525 mmol), neomenthyldiphenylphosphine (103 mg, 0.317 mmol), and 1,4-dioxane (25 mL) were charged to a 100-mL Hastelloy B autoclave. The autoclave was set up in the hood and purged with CO (3×200 psig). The autoclave was then pressured to 700 psig with CO and the mixture was heated to 110° C. for 3 hours. The CO pressure was kept at 900–1000 psig. The result of quantitative GC analysis is shown in Table 3.

COMPARATIVE EXAMPLE 3

The procedure of Example 3 was repeat except that $Ph_3$ (85.0 mg, 0.324 mmol) was used as the ligand. The result of quantitative GC analysis is shown in Table 3.

EXAMPLE 4

1-(4-isobutylphenyl)ethanol (10.0 g, 94.0 wt %, 52.7 mmol), 10% HCl (25.0 g), Pd(neomenthyldiphenylphosphine)$_4$ (520 mg, 0.370 mmol), and benzene (27 mL) were charged to a 300-mL Hastelloy B autoclave. The autoclave was set up in the hood and purged with $N_2$ (2×150 psig) and CO (2×150 psig). The autoclave was then pressured to 800 psig with CO and the mixture was heated to 125–129° C. for 6 hours. The result of quantitative GC analysis is shown in Table 4.

COMPARATIVE EXAMPLE 4

The procedure of Example 4 was repeated except that Pd(Ph$_3$P)$_4$ (428 mg, 0.370 mmol) was used as the catalyst. The result of quantitative GC analysis is shown in Table 4.

TABLE 1

|  | Example 1 | Comparative Example 1 |
| --- | --- | --- |
| 1-ethyl-4-isobutylbenzene | 0.06 | 0.12 |
| 4-isobutylstyrene | 0.0 | 0.05 |
| 1-chloro-1-(4-isobutylphenyl)ethane | 0.0 | 0.12 |
| 1-(4-isobutylphenyl)ethanol | 0 | 0.12 |
| 2-(4-isobutylphenyl)propionic acid | 93.0 | 85.3 |
| 3-(4-isobutylphenyl)propionic acid | 0.28 | 3.65 |
| Heavy ends | 0.50 | 0.63 |
| Total closure | 93.9 | 90.0 |
| Branched/linear | 338 | 23 |

TABLE 2

|  | Example 2 | Comparative Example 2 |
| --- | --- | --- |
| 1-ethyl-4-isobutylbenzene | 0.10 | 0.69 |
| 4-isobutylstyrene | 1.2 | 0.10 |
| 1-chloro-1-(4-isobutylphenyl)ethane | 3.5 | 0.77 |
| 1-(4-isobutylphenyl)ethanol | 0.22 | 0.15 |
| 2-(4-isobutylphenyl)propionic acid | 89.8 | 94.3 |
| 3-(4-isobutylphenyl)propionic acid | 0.16 | 3.5 |
| Heavy ends | 1.0 | 0.56 |
| Total closure | 95.9 | 100.1 |
| Branched/linear | 588 | 26 |

TABLE 3

|  | Example 3 | Comparative Example 3 |
| --- | --- | --- |
| 1-ethyl-4-isobutylbenzene | 0.10 | 0.33 |
| 4-isobutylstyrene | 0.70 | 0.19 |
| 1-chloro-1-(4-isobutylphenyl)ethane | 0.55 | 0.50 |
| 1-(4-isobutylphenyl)ethanol | 1.7 | 1.3 |
| 2-(4-isobutylphenyl)propionic acid | 90.4 | 85.8 |
| 3-(4-isobutylphenyl)propionic acid | 0.15 | 4.0 |
| Heavy ends | 2.1 | 1.6 |
| Total closure | 95.7 | 93.7 |
| Branched/linear | 592 | 21 |

TABLE 4

|  | Example 4 | Comparative Example 4 |
| --- | --- | --- |
| 1-ethyl-4-isobutylbenzene | 0.86 | 2.5 |
| 4-isobutylstyrene | 0.59 | 0.62 |
| 1-chloro-1-(4-isobutylphenyl)ethane | 2.2 | 3.7 |
| 1-(4-isobutylphenyl)ethanol | 1.0 | 2.0 |
| 2-(4-isobutylphenyl)propionic acid | 84.4 | 45.9 |
| 3-(4-isobutylphenyl)propionic acid | 0.64 | 34.3 |
| Heavy ends | 11.9 | 11.4 |
| Total closure | 101.6 | 100.4 |
| Branched/linear | 132 | 1.3 |

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with perfornng a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was firrt contacted, blended or mixed with one or more other substances, components and/or ingredients in accordance with the present disclosure. Without limiting the generality of the foregoing, as an illustrative example, where a claim specifies that a catalyst is a palladium compound in combination with a tertiary phosphine ligand, this phraseology refers to the makeup of the individual substances before they are combined and/or mixed separately or concurrently with one or more other materials, and in addition, at the time the catalyst is actually performing its catalytic function it need not have its original makeup—instead whatever transformations, if any, that occur in situ as the catalytic reaction is conducted is what the claim is intended to cover. Thus the fact that a substance, component or ingredient may have lost its original identity through a chemical reaction or transfonnation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented herein above. Rather, what is intended to be covered is as set forth in the ensuing claims and the equivalents thereof permitted as a matter of law.

What is claimed is:

1. A process of regioselectively producing an aromatic-substituted aliphatic acid or ester in which the aromatic group is bonded to the alpha-carbon atom of the aliphatic acid or ester moiety, which process comprises
   a) forming a mixture from ingredients comprising
      (i) an aromatic substituted alcohol and/or an aromatic substituted alkyl halide of the formula

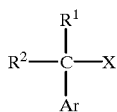

where X is a halogen atom or a hydroxy group, $R^1$ is hydrogen and $R^2$ is a $C_1$ to $C_6$ alkyl group;
      (ii) a copper-free palladium catalyst comprising a palladium compound compound in which the palladium has a valence of zero to two, and a cycloalkyldiarylphosphine of the formula

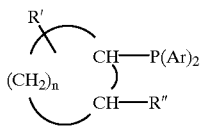

wherein R' and R" are the same or different and are individually hydrogen, alkyl, aryl or substituted aryl; Ar is phenyl, naphthyl, substituted phenyl or substituted naphthyl; and n is an integer from 3 to 6; and
      (iii) optionally a halogen acid; and
   b) heating said mixture with carbon monoxide at a pressure in the range of about 250 to about 2000 psig and a temperature in the range of from about 85° C. to about 150° C. for a period in the range of about 1 to about 8 hours to form said aromatic-substituted aliphatic acid or ester with a selectivity of at least 100:1 relative to the corresponding aromatic-substituted aliphatic acid or ester in which the aromatic group is bonded to the beta-carbon atom of the aliphatic acid or ester moiety.

2. A process according to claim 1 in which an aromatic substituted alcohol is used, in which the alcohol moiety of the aromatic substituted alcohol is ethanol, and in which the aromatic substituent of the aromatic substituted ethanol is bound to the 1-position of the ethanol.

3. A process according to claim 1 in which an aromatic substituted alcohol is used, and the aromatic substituent of the aromatic substituted alcohol is bound to the 1-position of the alcohol.

4. A process according to claim 1 in which an aromatic substituted alkyl halide is used, in which the alkyl halide moiety of the aromatic substituted alkyl halide is ethyl chloride, and in which the aromatic substituent of the aromatic substituted ethyl chloride is bound to the 1-position of the ethyl chloride.

5. A process according to claim 1 in which an aromatic substituted alkyl halide is used, in which the alkyl halide moiety of the aromatic substituted alkyl halide is ethyl bromide, and in which the aromatic substituent of the aromatic substituted ethyl bromide is bound to the 1-position of the ethyl bromide.

6. A process according to claim 1 in which an aromatic substituted alkyl halide is used, and the aromatic substituent of the aromatic substituted alkyl halide is bound to the 1-position of the alkyl halide.

7. A process according to claim 1 in which the aromatic group of the aromatic substituted alcohol and/or aromatic substituted alkyl halide is a heteroaryl group.

8. A process according to claim 1 in which the aromatic group of the aromatic substituted alcohol and/or aromatic substituted alkyl halide is a substituted aryl group.

9. A process according to claim 1 in which the aromatic group of the aromatic substituted alcohol and/or aromatic substituted alkyl halide is a methoxynaphthyl group.

10. A process according to claim 1 in which the aromatic group of the aromatic substituted alcohol and/or aromatic substituted alkyl halide is an isobutylphenyl group.

11. A process according to claim 1 in which an aromatic substituted alcohol is used, and the aromatic substituted alcohol is 1-(4-isobutylphenyl)ethanol.

12. A process according to claim 1 in which an aromatic substituted alkyl halide is used, and the aromatic substituted alkyl halide is 1-(4-isobutylphenyl)ethyl chloride.

13. A process according to claim 1 in which an aromatic substituted alcohol is used, and the aromatic substituted alcohol is 1-(6-methoxy-2-naphthyl)ethanol.

14. A process according to claim 1 in which an aromatic substituted alkyl halide is used, and the aromatic substituted alkyl halide is 1-(6-methoxy-2-naphthyl)ethyl bromide.

15. A process according to claim 1 in which the palladium compound(s) has a valence of two.

16. A process according to claim 1 in which the palladium compound is an inorganic palladium salt.

17. A process according to claim 1 in which the palladium compound is palladium dichloride.

18. A process according to claim 1 in which the cycloalkyl group of the cycloalkyldiarylphosphine ligand is a six-membered ring.

19. A process according to claim 1 in which the cycloalkyl group of the cycloalkyldiarylphosphine ligand is a neomenthyl group.

20. A process according to claim 1 in which both aryl groups of the cycloalkyldiarylphosphine ligand are phenyl groups.

21. A process according to claim 1 in which the cycloalkyldiarylphosphine ligand is neomenthyldiphenylphosphine.

22. A process according to claim 1 in which the cycloalkyldiarylphosphine ligand is neomentlhydiphenylphosphine and the palladium compound has a valence of two.

23. A process according to claim 22 in which the palladium compound is palladium dichloride.

24. A process according to claim 1 in which the ratio of cycloalkyldiarylphosphine ligand to palladium compound ranges from at least about 1:1 to about 20:1.

25. A process according to claim 1 in which the palladium catalyst is formed in the reaction mixture.

26. A process according to claim 1 in which the ratio of aromatic substituted alcohol and/or aromatic substituted alkyl halide to palladium compound is at least about 100:1.

27. A process according to claim 26 in which an aromatic substituted alcohol is used, and the aromatic substituted alcohol is a 1-substituted ethanol.

28. A process according to claim 27 in which the cycloalkyldiarylphosphine ligand is neomenthyldiphenylphosphine and the palladium compound has a valence of two.

29. A process according to claim 26 in which an aromatic substituted alkyl halide is used, and the aromatic substituted alkyl halide is a 1-substituted ethyl halide.

30. A process according to claim 29 in which the cycloalkyldiarylphosphine ligand is neomenthyldiphenylphosphine and the palladium compound has a valence of two.

31. A process according to claim 1 in which the halogen acid is used, and is hydrochloric acid.

32. A process according to claim 1 in which the halogen acid is used, and the halogen concentration is up to about 30 weight percent.

33. A process according to claim 1 in which said selectivity is at least 500:1.

34. A process according to claim 1 in which ingredient (i) is 1-(4-isobutylphenyl)ethanol or 1-(4isobutylphenyl)ethyl chloride, 1-(3-fluoro-4-biphenylyl)ethanol or 1-(3-fluoro-4-biphenylyl)ethyl bromide, 1-(6-methoxy-2-naphthyl) ethanol or 1-(6-methoxy-2-naphthyl)ethyl chloride, 1-(3-phenoxyphenyl)ethanol or 1-(3-phenoxyphenyl)ethyl bromide, or 1-(3-benzoylphenyl)ethanol or 1-(3-benzoylphenyl)ethyl chloride, or 1-(6-chloro-2-carbazolyl) ethyl bromide, or 1-(6-chloro-2-carbazolyl)ethanol.

35. A process according to claim 34 in which ingredient (i) is 1-(4-isobutylphenyl)ethanol or 1-(4-isobutylphenyl) ethyl chloride; in which the cycloalkyldiarylphosphine ligand is neomenthyldiphenylphosphine; in which the halogen acid is used; in which the halogen acid used is hydrochloric acid; in which the halogen concentration is up to about 30 w %; and in which said selectivity is at least 500:1.

* * * * *